United States Patent
Proksa et al.

(10) Patent No.: US 11,166,691 B2
(45) Date of Patent: Nov. 9, 2021

(54) AGENT IMAGING

(75) Inventors: Roland Proksa, Neu Wulmstorf (DE); Ladislav Jankovic, Fishkill, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 329 days.

(21) Appl. No.: 14/124,822

(22) PCT Filed: Jun. 12, 2012

(86) PCT No.: PCT/IB2012/052962
§ 371 (c)(1),
(2), (4) Date: Dec. 9, 2013

(87) PCT Pub. No.: WO2012/176093
PCT Pub. Date: Dec. 27, 2012

(65) Prior Publication Data
US 2014/0121510 A1   May 1, 2014

Related U.S. Application Data

(60) Provisional application No. 61/498,634, filed on Jun. 20, 2011.

(51) Int. Cl.
*A61B 6/00* (2006.01)
*A61B 5/00* (2006.01)
*A61B 6/03* (2006.01)

(52) U.S. Cl.
CPC ........... *A61B 6/54* (2013.01); *A61B 5/0095* (2013.01); *A61B 6/032* (2013.01); *A61B 6/4417* (2013.01); *A61B 6/481* (2013.01); *A61B 6/507* (2013.01)

(58) Field of Classification Search
None
See application file for complete search history.

(56) References Cited

U.S. PATENT DOCUMENTS

| | | | |
|---|---|---|---|
| 5,301,672 A | | 4/1994 | Kalender |
| 6,662,040 B1 * | | 12/2003 | Henrichs et al. ............. 600/431 |
| 7,756,242 B2 | | 7/2010 | Kudo |
| 8,867,808 B2 | | 10/2014 | Satoh et al. |
| 2007/0222447 A1 * | | 9/2007 | Van Der Brink et al. .... 324/312 |

(Continued)

FOREIGN PATENT DOCUMENTS

| | | |
|---|---|---|
| JP | 3165257 | 7/1991 |
| JP | 2003010172 | 1/2003 |

(Continued)

OTHER PUBLICATIONS

Lihong V. Wang, "Prospects of PHotoacoustic tomography", Med. Phys, vol. 35, No. 12, Dec. 2008.*

(Continued)

*Primary Examiner* — Amelie R Davis
*Assistant Examiner* — Marjan Saboktakin
(74) *Attorney, Agent, or Firm* — Larry Liberchuk

(57) ABSTRACT

A system (200) includes a first imaging system (201) that utilizes first radiation to image an interior region of interest of a subject, including a first agent in the region of interest and a second imaging system (218) that utilizes second radiation to image a second agent in the region of interest, wherein an output of the second imaging system is used to trigger the first imaging system to scan the region of interest, including the first agent in the region of interest.

16 Claims, 5 Drawing Sheets

(56) References Cited

U.S. PATENT DOCUMENTS

| | | | |
|---|---|---|---|
| 2007/0258896 A1* | 11/2007 | Nachaliel | 424/9.1 |
| 2007/0258908 A1 | 11/2007 | Lanza et al. | |
| 2009/0187099 A1* | 7/2009 | Burcher | 600/430 |
| 2010/0196278 A1 | 8/2010 | Tomida | |
| 2010/0249570 A1 | 9/2010 | Carson et al. | |
| 2010/0324422 A1 | 12/2010 | Wanda et al. | |
| 2011/0117028 A1* | 5/2011 | Zharov | A61B 5/0059 |
| | | | 424/9.36 |

FOREIGN PATENT DOCUMENTS

| | | | |
|---|---|---|---|
| JP | 2005073764 | * | 8/2003 |
| JP | 2005073764 | | 3/2005 |
| WO | 2005106519 A1 | | 11/2005 |
| WO | 2009057019 A1 | | 5/2009 |
| WO | 2010/024290 | | 3/2010 |
| WO | 2010135469 A1 | | 11/2010 |

OTHER PUBLICATIONS

Park et al. Photoacoustic Imaging Using Array Transducer, Proc. Of SPIE vol. 6437, 643714.*

Kostli, et al., Two-dimensional photoacoustic imaging by use of Fourier-transform image reconstruction and a detector with an anisotropic response, Applied Optics, Apr. 1, 2003, pp. 1899-1908, vol. 42, No. 10, Optical Society of America.

Park, et al, Photoacoustic Imaging Using Array Transducer, Photons Plus Ultrasound:Imaging and Sensing 2007, 2007, pp. 643714-1-643714-7, vol. 6437, Proc. of SPIE.

Jankovic, et al., In Vivo Photoacoustic Imaging of Nude Mice Vasculature Using a Photoacoustic Imaging System Based on a Commercial Ultrasound Scanner, pp. 68560N-1-68560N-12, vol. 6856, Proc. of SPIE.

Jankovic, et al., A Modified Commercial Ultrasound Scanner used for In-Vivo Photoacoustic Imaging of Nude Mice Injected with Non-Targeted Contrast Agents, pp. 68560O-1-68560O-9, vol. 6856, Proc. of SPIE.

* cited by examiner

AGENT IMAGING

CROSS REFERENCE TO RELATED APPLICATIONS

This application is a national filing of PCT application Serial No. PCT IB2012/052962, filed Jun. 12, 2012, published as WO 2012/176093 A1 on Dec. 27, 2012, which claims the benefit of U.S. provisional application Ser. No. 61/498,634 filed Jun. 20, 2011, which is incorporated herein by reference.

FIELD OF THE INVENTION

The following generally relates to imaging and is described with particular application to agent based computed tomography (CT); however, the following is also amenable to other imaging modalities.

BACKGROUND OF THE INVENTION

Contrast enhanced CT is an imaging technique which captures the transit of an administered radio-contrast material through vascular tissue of interest such as a vessel and/or an organ like the heart or the brain. Generally, for contrast enhanced CT, a bolus of a radio-contrast material is intravenously administered to a patient, and a region of interest of the patient that includes the vascular tissue of interest is scanned. The radio-contrast material causes the x-ray density in the vascular tissue of interest to temporarily increase as the radio-contrast material flows through the vascular tissue, resulting in enhanced data.

Analysis of the rustling CT data can be used to determine a health state of the vascular tissue of interest. For cardiac applications, this may include quantifying the radio-contrast material distribution in the cardiac muscle over time. Such analysis may include determining parameters such as blood flow, blood volume, mean transit time, maximum upslope, time to peak, etc. This information can be used to identify ischemic (dead) tissue and/or differentiate between irreversibly damaged (necrotic) and potentially reversibly damaged (or at-risk) tissue.

To capture peak contrast material uptake, scanning needs to be synchronized with contrast material administration. FIG. 1 shows an example contrast material profile 102, including uptake 104, peak uptake 106 and wash out 108 regions, as a function of time. FIG. 1 also shows a pre (or baseline) contrast region 110 and a post contrast region 112. In FIG. 1, a y-axis 114 represents the amount of contrast material and an x-axis 116 represents time. If synchronization is off, the scan may be performed too early or before contrast material reaches the tissue, too late or after the contrast material leaves the tissue, or while contrast material is in the tissue, but not during peak uptake.

However, timing scanning with administration of a contrast material bolus can be difficult. Solutions for determining the timing are bolus tracking and test bolus injection. In bolus tracking, a 2D axial slice is continuously imaged and the contrast material level in a vessel is tracked until the level reaches a threshold, which triggers data acquisition. In test bolus injection, a low concentration test bolus is used to measure the bolus arrival time in a similar manner. The measured time is then used to trigger subsequent data acquisition after administration of the examination bolus.

CT scanners emit ionizing radiation and thus expose the person being scanned to ionizing radiation, which may damage or kill cells and/or increase the risk of cancer. Unfortunately, both bolus tracking and test bolus injection require additional CT imaging to determine when to determine when to trigger the contrast enhanced CT scan. In view of at least the above, there is an unresolved need for other approaches for determining the timing of scanning with respect to the administration of a contrast material bolus.

SUMMARY OF THE INVENTION

Aspects of the present application address the above-referenced matters and others.

According to one aspect, a system includes a first imaging system that utilizes first radiation to image an interior region of interest of a subject, including a first agent in the region of interest and a second imaging system that utilizes second radiation to image a second agent in the region of interest, wherein an output of the second imaging system is used to trigger the first imaging system to scan the region of interest, including the first agent in the region of interest.

In another aspect, a method includes detecting a presence of a photo-acoustic agent in tissue of interest and triggering a scan in response to detecting the presence of the photo-acoustic agent in tissue of interest.

In another aspect, a computer readable instructions encoded on computer readable medium, which, when executed by a processor of a computing system causes the processor to: trigger a scan of a region of interest based on an identification of a presence of a photo-acoustic agent in the region of interest.

Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
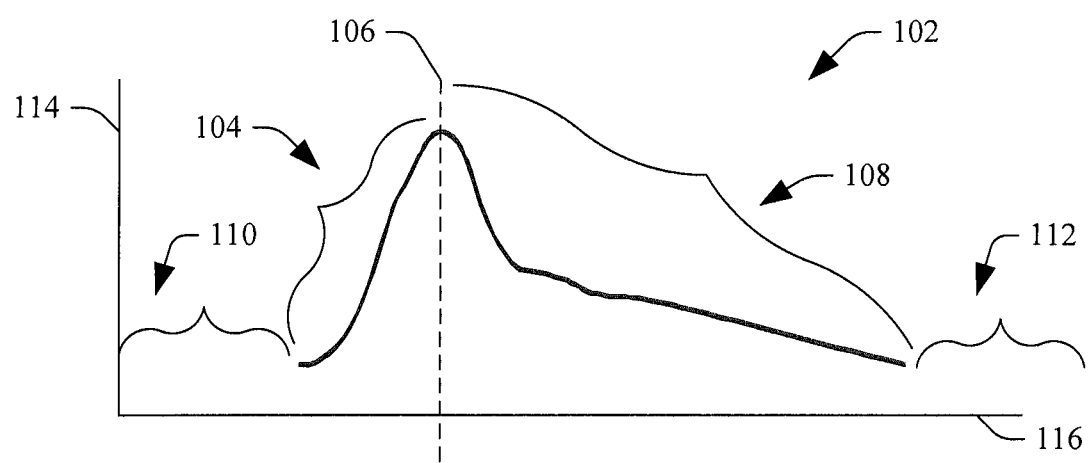
FIG. 1 schematically illustrates an example contrast profile.
Figure 2:
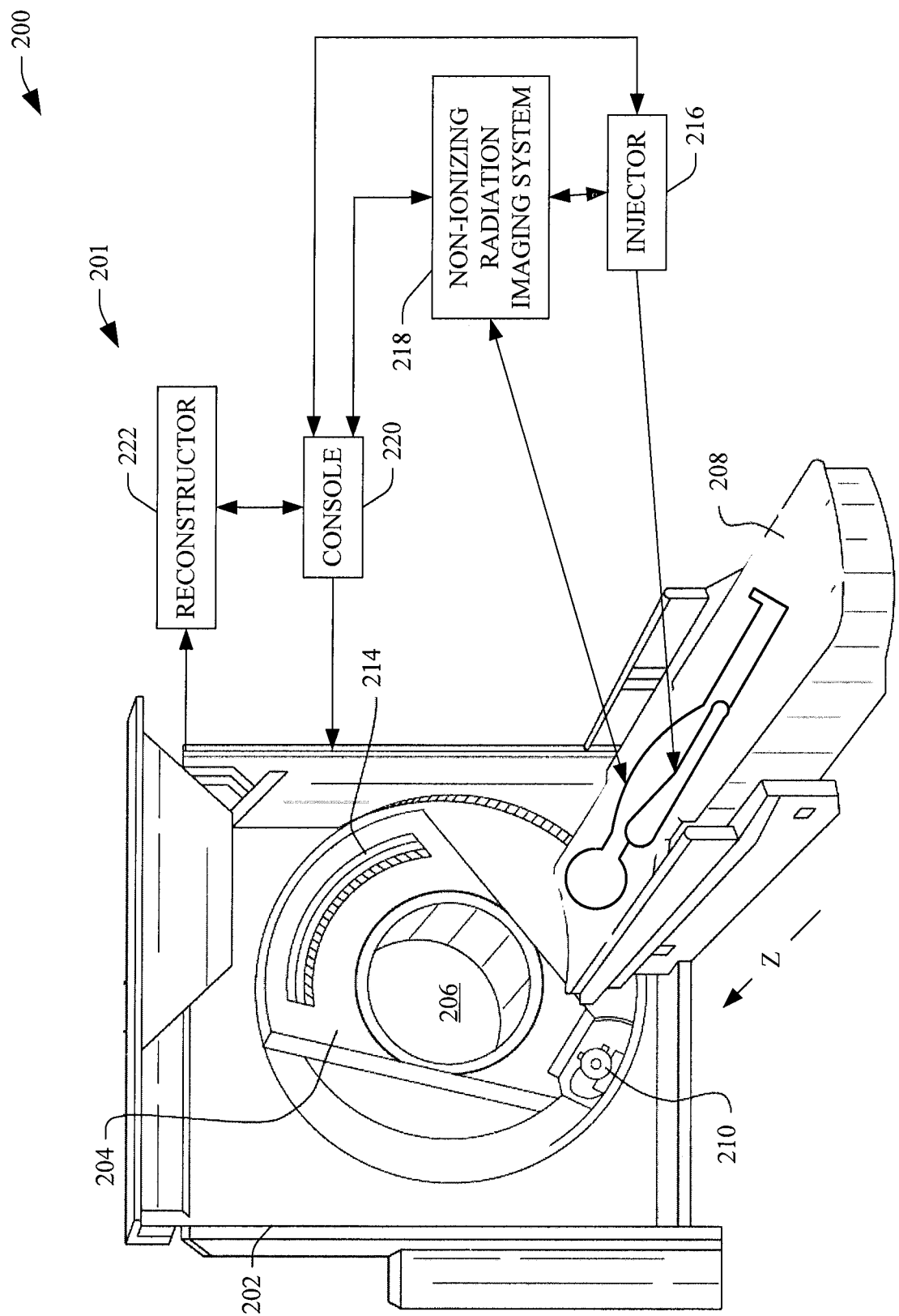
FIG. 2 schematically illustrates an example system including an ionizing radiation imaging system and a non-ionizing radiation imaging system.

FIG. 2 illustrates an example system 200, which includes an ionizing radiation imaging system 201 such as a computed tomography (CT) scanner and a non-ionizing radiation imaging system 218.

The ionizing radiation imaging system 201 includes a generally stationary gantry 202 and a rotating gantry 204, which is rotatably supported by the stationary gantry 202. The rotating gantry 204 rotates around an examination region 206 about a longitudinal or z-axis.

A radiation source 210, such as an x-ray tube, is supported by and rotates with the rotating gantry 204, and emits first or ionizing radiation. A radiation sensitive detector array 214 is located opposite the source 210, across the examination region 206. The detector array 214 detects radiation that traverses the examination region 206 and generates an electrical signal indicative thereof.

A subject support 208 such as a couch supports a subject or object in the examination region 206.

An injector 216 is configured to inject various agents such as a targeted agent and/or a contrast agent/material for an imaging procedure. A suitable contrast material includes a radio-contrast material (e.g., for a contrast enhanced imaging procedure), a non radio-contrast material (e.g., a photo-acoustic or contrast material) and/or other contrast material. Where the contrast material is manually administered, the injector 216 can be omitted.

The non-ionizing radiation imaging system 218 emits a non-ionizing excitation signal that excites certain non radio-contrast materials (e.g., a photo-acoustic or other contrast material), which emit characteristic radiation (e.g., acoustic or other) in response to being excited thereby. The non-ionizing radiation imaging system detects the characteristic radiation and generates a signal indicative thereof.

A general purpose computer serves as an operator console 220. The console 220 includes a human readable output device such as a monitor or display and an input device such as a keyboard and mouse. Software resident on the console 220 allows the operator to interact with the scanner 200. Such interaction includes selecting an imaging protocol like a contrast enhanced protocol, which may include actuating the injector 218 and initiating scanning, based on the signal indicative of the characteristic radiation, etc.

A reconstructor 222 reconstructs the signal and generates three dimensional (3D) volumetric image data.

As described in greater detail below, detection of a presence of the non radio-contrast material, based on the signal indicative of the characteristic radiation in a region of interest, can be used to trigger the console 220 to initiate a contrast enhanced CT scan via the imaging system 201. This allows for initiating a contrast enhanced CT scan without exposing the patient to ionizing radiation in addition to the ionizing radiation exposure from the contrast enhanced CT scan, such as when using bolus tracking or test bolus injection, which both exposes the patient to additional radiation to determine when to trigger the CT scan.

Figure 3:
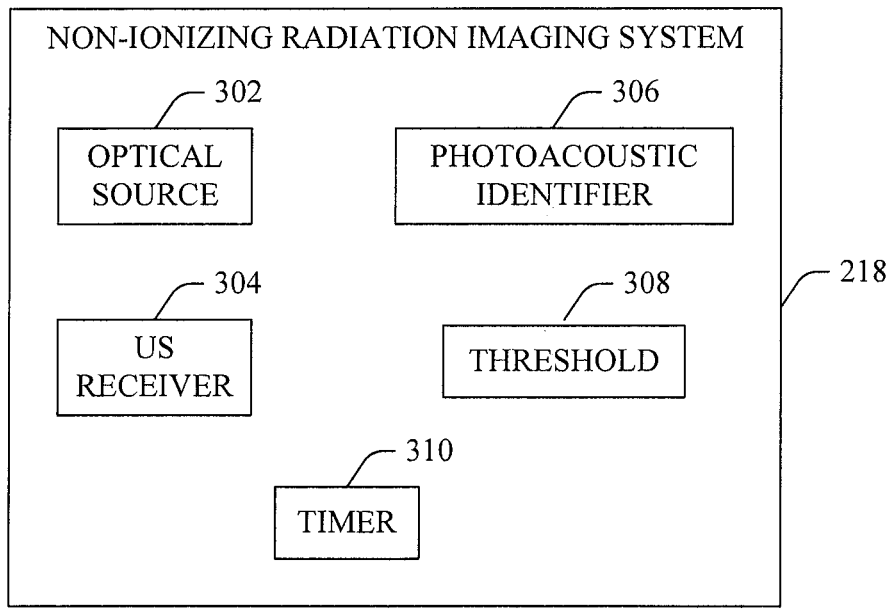
FIG. 3 schematically illustrates an example in which the non-ionizing radiation imaging system is configured for photo-acoustic imaging.

FIG. 3 schematically illustrates an example of the non-ionizing radiation imaging system 218. For this example, the non radio-contrast material includes a photo-acoustic contrast material. A suitable photo-acoustic contrast material includes indocyanine green (ICG), methylene blue and/or other contrast material that absorbs an optical signal and emits an acoustic signal in response thereto.

The non-ionizing radiation imaging system 218 includes an optical source 302 such as a laser. A suitable laser for use with methylene blue includes a six hundred and sixty-five nanometer (665 nm) laser configured to emit short (e.g., five to ten nanosecond (5-10 ns) pulse, which can penetrate the subject and be absorbed by the photo-acoustic contrast material, which excites or stimulates the photo-acoustic contrast material to emit an acoustic signal.

For ICG an eight hundred and five nanometers (805 nm) laser wavelength would be used, for example. In another embodiment, a multi-wavelength laser is utilized. Multi-wavelength laser irradiation can be used to distinguish spectral features of the contrast agent from the background.

An ultrasound (US) receiver 304 is configured to detect the acoustic signal emitted by from the excited or stimulated photo-acoustic contrast material. The US receiver 304 generates a signal indicative of the received acoustic signal. In FIG. 3, the US receiver 304 is a single pixel detector without any spatial encoding capabilities. In other embodiments, the US receiver 304 may include more than one pixel detector and/or include spatial encoding capabilities.

A photo-acoustic identifier 306 identifies a presence or absence of the photo-acoustic contrast material in tissue of interest based on the signal generated by the US receiver 304 and generates a trigger signal when the signal indicates photo-contrast material is present in the region of interest. In one non-limiting instance, the photo-acoustic identifier 306 compares the signal (e.g., strength, intensity, etc.) with a reference threshold 308 and generates the trigger signal when the signal satisfies the threshold. The reference threshold can be determined based on the output of the acoustic detector 304 when no photo-acoustic contrast material has been administered or otherwise. The photo-acoustic identifier 306 conveys the trigger signal to the console 220.

A timer 310 can be used to measure a time duration from administration of the photo-acoustic contrast material to identification of a presence of photo-acoustic contrast material in the tissue of interest. The timer 310 can be started based on a signal from the injector 216 and/or console 220 indicating the photo-acoustic contrast material has been administered and/or by a technician or other authorized personnel. The timer 310 conveys the timer duration to the console 220. In another embodiment, the timer 310 is omitted.

Figure 4:
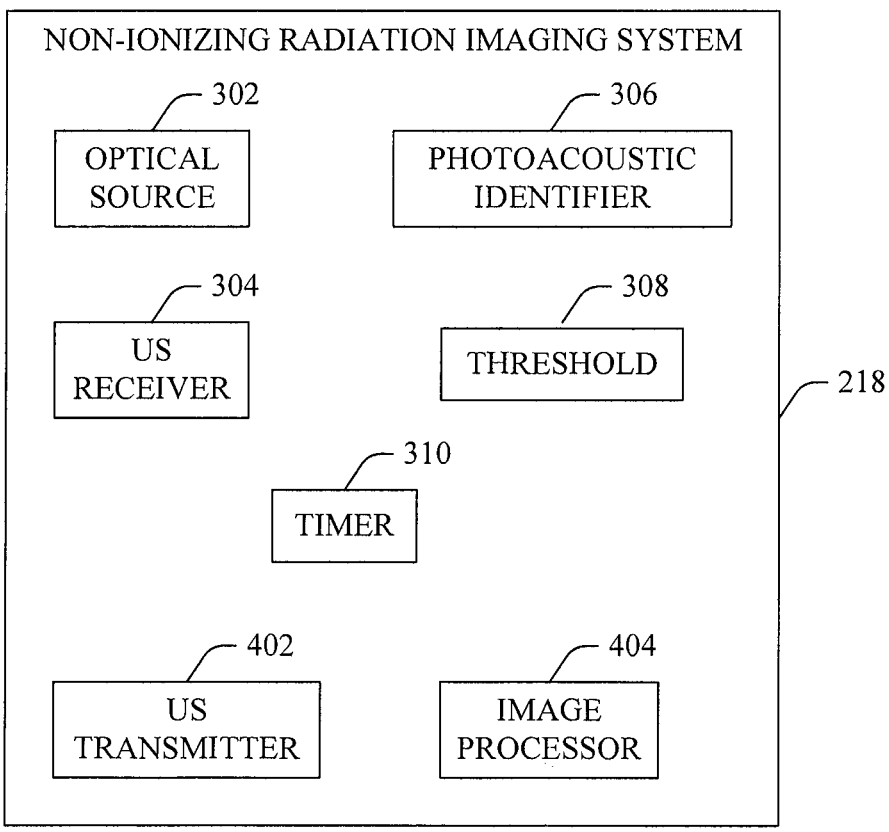
FIG. 4 schematically illustrates an example in which the non-ionizing radiation imaging system is further configured for ultrasound imaging.

FIG. 4 schematically illustrates an embodiment which is substantially similar to that of FIG. 3, except that the non-ionizing radiation imaging system 218 further includes an ultrasound (US) transmitter 402 and an image processor 404. The ultrasound (US) transmitter 402 emits high frequency (e.g., one to twenty megahertz (1-20 MHz)) broad-band acoustic waves via one or more transducer elements, which penetrate the subject and are attenuated and returned (as echoes) as they traverse the structure based on the composition of the structure. The ultrasound (US) receiver 304 is also configured to detect the echoes and generate signals indicative thereof. In this embodiment, the US receiver 304 includes a one or two dimensional array of pixel detectors.

The image processor 404 processes the signals indicative of the echoes and generates structural ultrasound images based thereon. Suitable processing includes conventional B-mode delay and sum processing and/or other processing. The processor 404 also processes the acoustic signal and generates images indicative of the photo-acoustic contrast material. The processor 404 superimposes or overlays the structural and the photo-acoustic contrast material images, with the resulting combined image showing the photo-acoustic contrast material in the context of the scanned structural information. One or more of the images can be visually presented via a display of the non-ionizing radiation source 218, the console 220, and/or other display.

Variations are contemplated.

In FIGS. 3 and 4, the photo-acoustic identifier 306 and/or the timer 310 are located in the non-ionization radiation source 218. In another embodiment, one or more of these components is located in the console 220 and/or other device.

In FIG. 4, the US transmitter 402 and image processor 404 are located in the non-ionization radiation source 218. In another embodiment, one or more of these components is located in a separate US device and/or other device.

In another embodiment, a user of the system 202 visually observes the trigger signal and manually initiates the CT scan.

In another embodiment, a user of the system 202 visually observes the generated images and manually initiates the CT scan.

In another embodiment, where the non-ionizing radiation imaging system 218 is used to determine the timing between the administration of a radio-contrast and a contrast enhanced CT scan for a subsequent CT scan, the non-ionizing radiation imaging system 218 and the ionizing radiation imaging system 201 can be located in separated examination rooms.

In another embodiment, the non-ionizing radiation imaging system 218 includes a microwave source which is used to emit electromagnetic radiation that excites a corresponding administered non radio-contrast to emit characteristic radiation. Likewise, detecting the characteristic radiation in the region of interest can be used to trigger a contrast enhanced CT scan of the region of interest.

Figure 5:
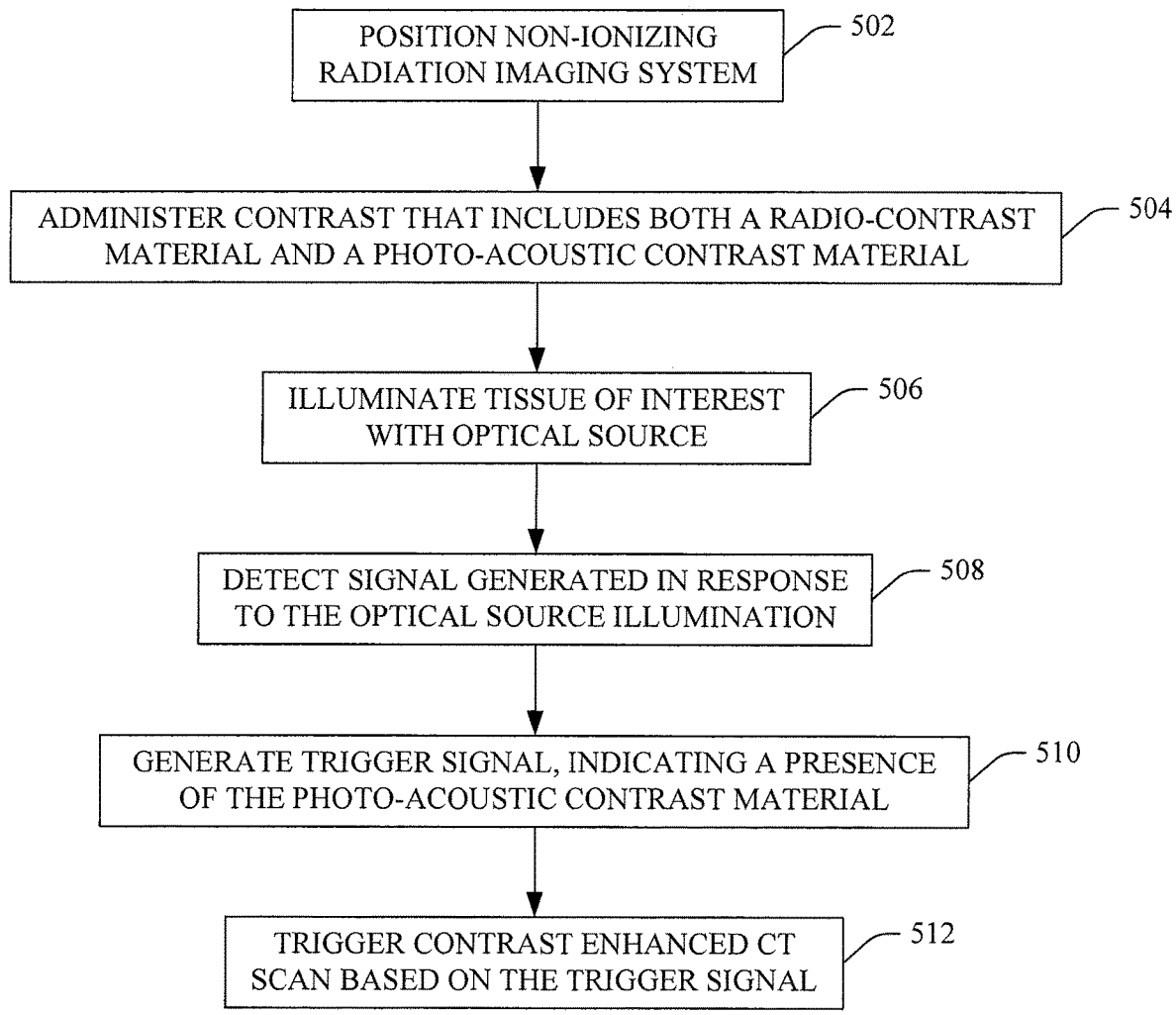
FIG. 5 illustrates an example method for triggering a contrast enhanced CT scan.

FIG. 5 illustrates a method for triggering a contrast enhanced CT scan after administration of a contrast bolus.

It is to be appreciated that the ordering of the below acts is for explanatory purposes and not limiting. As such, other orderings are also contemplated herein. In addition, one or more of the acts may be omitted and/or one or more other acts may be included.

At 502, the non-ionizing radiation imaging system 218 is positioned with respect to a patient so that a presence of a photo-acoustic contrast material can be detected in tissue of interest.

The tissue of interest may be a vessel leading to or part of a region of interest to be scanned via the CT scanner 202 in connection with a contrast enhanced CT protocol. The non-ionizing radiation imaging system 218 may be held in place by a user, a robot, a mechanical device, etc.

At 504, a contrast material including both a radio-contrast material and a photo-acoustic contrast material is administered to the patient.

At 506, the non-ionizing radiation imaging system 218 is used to illuminate the tissue of interest with the optical source 302.

At 508, the non-ionizing radiation imaging system 218 is used to detect signals emitted from the photo-acoustic contrast material with the US receiver 304 and generate a signal indicative thereof.

At 510, the photo-acoustic identifier 306 generates a trigger signal in response to the signal from the US receiver 304 indicating a presence of photo-acoustic contrast material.

At 512, the console 220, in response to the trigger signal, invokes the system 202 to perform the CT scan, including capturing, at least, peak contrast uptake up the radio-contrast therein.

Figure 6:
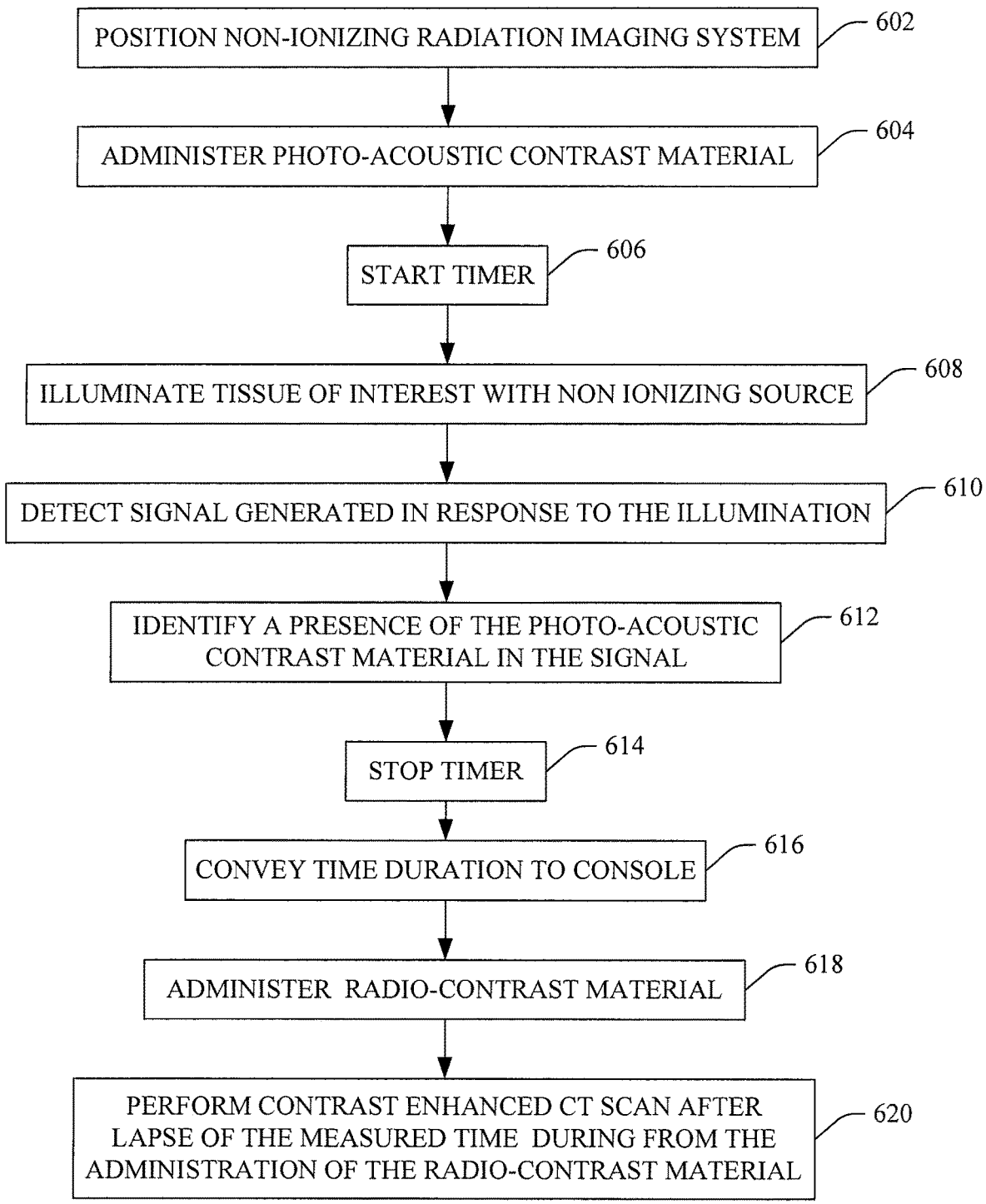
FIG. 6 illustrates an example method for determining timing for a contrast enhanced CT scan.

FIG. 6 illustrates a method determining timing for initiating CT scan subsequent to administration of a radio-contrast.

It is to be appreciated that the ordering of the below acts is for explanatory purposes and not limiting. As such, other orderings are also contemplated herein. In addition, one or more of the acts may be omitted and/or one or more other acts may be included.

At 602, the non-ionizing radiation imaging system 218 is positioned with respect to a patient so that a presence of a photo-acoustic contrast material can be detected in tissue of interest.

The tissue of interest may be a vessel leading to or part of a region of interest to be scanned via the CT scanner 202 in connection with a contrast enhanced CT protocol. The non-ionizing radiation imaging system 218 may be held in place by a user, a robot, a mechanical device, etc.

At 604, a contrast material only including a photo-acoustic contrast material is administered to the patient.

At 606, concurrently with act 604 (or just before or just after), the non-ionizing radiation imaging system 218 starts the timer 310.

At 608, the non-ionizing radiation imaging system 218 is used to illuminate the vessel with the optical source 302.

At 610, the non-ionizing radiation imaging system 218 is used to detect signals emitted from the photo-acoustic contrast material with the US receiver 304 and generate a signal indicative thereof.

At 612, the photo-acoustic identifier 306 identifies a presence of the photo-acoustic contrast material based on the signal.

At 614, the non-ionizing radiation imaging system 218, in response to the identification of the presence, stops the timer 310.

At 616, the non-ionizing radiation imaging system 218 conveys the time duration measured by the timer 306 to the console 220.

At 618, a contrast material including a radio-material for a contrast enhanced CT scan is administered to the patient.

At 620, the console 220 initiates the CT scan based on the measured time duration and the CT scanner scans the region of interest, capturing, at least, peak contrast uptake up the radio-contrast therein.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

It is to be appreciated that one or more of the components discussed herein (e.g., the photo-acoustic identifier 306, etc.) can be implemented via one or more processors executing one or more computer readable instructions encoded or embodied on computer readable storage medium such as physical memory which causes the one or more processors to carry out the various functions described herein and/or other functions. Additionally or alternatively, the one or more processors can execute instructions carried by transitory medium such as a signal or carrier wave.

Although the above has been described in connection with CT, it is to be appreciated that the imaging system may include other imaging applications such as agent based magnetic resonance imaging (MRI), agent based nuclear medicine (NM) imaging, and/or other imaging. Of course, the agent (e.g., Rubidium-82) for a particular modality (e.g., positron emission tomography (PET)) would correspond to that modality (e.g., PET). In the context of non-ionizing radiation imaging, detecting the agent as described herein can be utilized to determine and/or optimize scanning and/or workflow, for example, to identify a start scan time, an end scan time, etc.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A system for determining when to start scanning a subject with respect to an administration of an ionizing contrast agent, comprising:
   a first imaging system configured to image and contrast the ionizing contrast agent in a predetermined area of a vessel in the subject utilizing an ionizing radiation; and
   a second imaging system configured to image and contrast a photo-acoustic contrast agent in the predetermined area of the vessel utilizing a non-ionizing radiation, wherein the second imaging system comprises:
      an optical source configured to emit the non-ionizing radiation that penetrates tissues of the subject and excites the photo-acoustic contrast agent;
      an ultrasound receiver configured to detect acoustic radiation in the predetermined area of the vessel emitted in response to the non-ionizing radiation and output an acoustic signal representative of the detected acoustic radiation in the predetermined area of the vessel; and
      at least one processor configured to receive the acoustic signal, compare the acoustic signal to a predetermined threshold, and generate a trigger signal indicative of a presence of the photo-acoustic contrast agent in the predetermined area of the vessel when the acoustic signal exceeds the predetermined threshold, wherein the first imaging system is further configured, in response to the generated trigger signal, to start scanning the predetermined area of the vessel.

2. The system of claim 1, wherein the non-ionizing radiation includes non-ionizing pulses of wavelengths that penetrate the subject to excite the photo acoustic contrast agent in the predetermined area of the vessel.

3. The system of claim 1, wherein the ultrasound receiver is a single pixel detector without spatial encoding that detects the acoustic radiation emitted from the photo-acoustic contrast agent present in the predetermined area of the vessel.

4. The system of claim 1, wherein the second imaging system further comprises:
   a timer configured to measure a time duration from an administration of the photo-acoustic contrast agent to the detected acoustic radiation in the predetermined area of the vessel based on the received acoustic signal; and
   wherein the first imaging system is triggered to start scanning the predetermined area of the vessel after lapse of the measured time duration from the administration of the ionizing contrast agent.

5. The system of claim 1, wherein the non-ionizing radiation includes a plurality of wavelengths that distinguish the photo-acoustic contrast agent from background in an image generated by the second imaging system.

6. The system of claim 1, wherein the photo-acoustic agent includes an indocyanin green based contrast material.

7. The system of claim 1, wherein the first imaging system captures a peak uptake of the ionizing contrast agent during a scan of the predetermined area of the vessel.

8. The system of claim 1, wherein the ionizing contrast agent is a radio-agent, and the photo-acoustic contrast agent is methylene blue.

9. A method for determining when to start scanning a subject with respect to an administration of an ionizing contrast agent, comprising:
   illuminating a predetermined area of a vessel in the subject with a non-ionizing radiation that penetrates the subject to excite a photo-acoustic contrast agent in the predetermined area of the vessel, wherein the excited photo-acoustic contrast agent emits an acoustic radiation in response to the penetrating non-ionizing radiation;
   detecting the acoustic radiation by an ultrasound receiver that scans the predetermined area of the vessel and generates an acoustic signal indicative of the detected acoustic radiation;
   detecting a presence of the photo-acoustic contrast agent in the predetermined area of the vessel by at least one processor based on the generated acoustic signal; and
   starting to scan the predetermined area of the vessel using an ionizing radiation system being triggered in response to the detected presence of the photo-acoustic contrast agent in the predetermined area of the vessel.

10. The method of claim 9, wherein the presence of the photo-acoustic contrast agent in the predetermined area of the vessel is detected when the photo-acoustic contrast agent in the predetermined area of the vessel exceeds a predetermined threshold.

11. The method of claim 9, further comprising generating a computed tomography (CT) image contrasting the ionizing contrast agent in the predetermined area of the vessel.

12. The method of claim 11, wherein the generated CT image captures a peak uptake of the ionizing contrast agent in the predetermined area of the vessel.

13. The method of claim 9, wherein the ultrasound receiver is a single pixel detector without spatial encoding.

14. The method of claim 9, further comprising generating a trigger signal indicative of the presence of the photo-acoustic contrast agent in the predetermined area of the vessel using the at least one processor;
   w receiving the trigger signal, and triggering the ionizing radiation system to start scanning the predetermined area of the vessel in response to the received trigger signal.

15. The method of claim 9, further comprising:
   measuring a time duration from an administration of the photo-acoustic contrast agent to the detected presence of the photo-acoustic contrast agent in the predetermined area of the vessel;
   wherein the triggered scanning uses an ionizing radiation after the administration of the ionizing contrast agent and a lapse of the measured time duration from the administration of the photo-acoustic contrast agent to the detected presence of the photo-acoustic contrast agent in the predetermined area of the vessel.

16. A non-transitory computer-readable medium having one or more executable instructions stored thereon, which, when executed by at least one processor, cause the at least one processor to perform a method for determining when to start scanning a subject with respect to an administration of an ionizing contrast agent, the method comprising:
   illuminating a predetermined area of a vessel in the subject with a non-ionizing radiation that penetrates the subject to excite a photo-acoustic contrast agent in the predetermined area of the vessel, wherein the excited photo-acoustic contrast agent emits an acoustic radiation in response to the penetrating non-ionizing radiation;

detecting the acoustic radiation by an ultrasound receiver that scans the predetermined area of the vessel and generates an acoustic signal indicative of the detected acoustic radiation;
detecting a presence of the photo-acoustic contrast agent in the predetermined area of the vessel based on the generated acoustic signal; and
starting to scan the predetermined area of the vessel using an ionizing radiation system being triggered in response to the detected presence of the photo-acoustic contrast agent in the predetermined area of the vessel.

* * * * *